United States Patent
Clemann et al.

(10) Patent No.: US 9,013,567 B2
(45) Date of Patent: Apr. 21, 2015

(54) METHOD FOR DETERMINING AGE, AND AGE-DEPENDENT SELECTION OF COSMETIC PRODUCTS

(75) Inventors: Sven Clemann, Hamburg (DE); Soeren Jaspers, Schenefeld (DE); Maximillian Wolde, Hamburg (DE); Gabriel Khazaka, Cologne (DE)

(73) Assignee: Courage + Khazaka Electronic GmbH, Cologne (DE)

( * ) Notice: Subject to any disclaimer, the term of this patent is extended or adjusted under 35 U.S.C. 154(b) by 754 days.

(21) Appl. No.: 13/380,308

(22) PCT Filed: Mar. 5, 2010

(86) PCT No.: PCT/EP2010/001367
§ 371 (c)(1),
(2), (4) Date: Aug. 16, 2012

(87) PCT Pub. No.: WO2010/149235
PCT Pub. Date: Dec. 29, 2010

(65) Prior Publication Data
US 2012/0300049 A1    Nov. 29, 2012

(30) Foreign Application Priority Data
Jun. 22, 2009   (DE) .......................... 10 2009 030 062

(51) Int. Cl.
H04N 7/18 (2006.01)
A61B 5/00 (2006.01)
A45D 44/00 (2006.01)

(52) U.S. Cl.
CPC ............ *A61B 5/0059* (2013.01); *A45D 44/005* (2013.01); *A45D 2044/007* (2013.01); *A61B 5/442* (2013.01)

(58) Field of Classification Search
None
See application file for complete search history.

(56) References Cited

U.S. PATENT DOCUMENTS 6,070,092 A * 5/2000 Kazama et al. ............... 600/310
2006/0239547 A1   10/2006 Robinson et al.

FOREIGN PATENT DOCUMENTS

WO   2008003146 A2   1/2008

OTHER PUBLICATIONS

Yuriy Vashpanov et al: "Multispectral images in polarized light for medical applications" Multisensor Fusion and Integration for Intelligent Systems, 2008, MFI 2008. IEEE International Conference on, IEEE, Piscataway, NJ, USA, Aug. 20, 2008, pp. 86-89.

* cited by examiner

*Primary Examiner* — Sath V Perungavoor
*Assistant Examiner* — Janese Duley
(74) *Attorney, Agent, or Firm* — Abel Law Group, LLP

(57) ABSTRACT

A method for determining the skin age of consumers and a device suitable for implementing the method. The skin age is determined by capturing a predetermined skin area optoelectronically. The image data obtained during capturing the skin area are stored in an intermediate memory. Thereafter the color distribution and/or the color space are determined by means of image analysis. The determination is performed integratively, the result also being stored in an intermediate memory.

17 Claims, 4 Drawing Sheets

METHOD FOR DETERMINING AGE, AND AGE-DEPENDENT SELECTION OF COSMETIC PRODUCTS

BACKGROUND OF THE INVENTION

1. Field of the Invention

The invention relates to a method and to a device suitable for the method for determining the age of consumers, which has the option of suggesting cosmetic products matched to the age.

2. Discussion of Background Information

The skin of a human changes over the course of a lifetime. At a young age, the skin generally presents itself as firm, smooth and evenly pigmented. With increasing age, this changes to a different extent from person to person.

Skin aging refers to the complex biological process of the change of the skin accompanying aging. Here, this does not only mean the chronological aging, but also the intrinsic aging, i.e. the genetically controlled reduced responsiveness of the skin cells. It cannot be influenced. In contrast to this, it is possible to influence the extrinsic factors (environmental factors such as UV light, chemical reagents, mechanical load). This is why in skin aging a distinction is made between the so-called "time aging" and the "environmental aging" (also referred to as "light aging"). Skin aging, which usually becomes visible in the form of wrinkles, starts at a different time from person to person; this can also be traced back to the lifestyle of the person: factors such as heat and coldness, stress, poor nutrition, and alcohol and nicotine consumption can accelerate the natural aging of the skin.

However, time aging of the skin is a result of exhausting the cell-division processes and undersupplying the cells. The skin develops deep wrinkles and furrows; its dry surface tends to tear and produce pseudo-scars; the epidermis becomes thinner, as a result of which the blood vessels appear even more prominently. The dryness of the old skin can be traced back to a reduced activity of the sebaceous glands: less fat is produced, the skin loses elasticity and is no longer as able to regenerate, which can, overall, even lead to wound-healing disorders.

For some people, time aging already starts in their mid-20s. The following text lists the most common symptoms of aging for different age groups. In this respect, it should be noted that these are only approximate values and do not apply to every person. The list relates to women—their aging begins approximately 10 years before that of men. However, in exchange, male skin aging proceeds more quickly.

From the age of 25 years old: the cell division already slows down at this age for some people. As a result of this, the epidermis becomes thinner and starts to lose its elasticity.

From the age of 30 years old: so-called glabellar lines can form between the eyes; they are brought about by our facial expressions. It is also possible for first nasolabial folds (wrinkles between nose and upper lip) to appear. Moreover, crow's feet form at the edge of the eyes. These are small lines which run toward the eyes and are the first visible sign of skin aging in many humans.

From the age of 40 years old: so-called crease lines appear in the face, which are small wrinkles that—as the name indicates—give the affected person a creased look. Other, already present wrinkles deepen and the skin starts to lose a lot of moisture. In women, the menopause—the end of menstruation—leaves its mark. The production of the estrogen hormone is reduced, and this has a number of consequences: amongst others, the skin becomes thinner and more sensitive.

From the age of 50 years old: the skin tension is reduced further. Liver spots appear; in these, the skin pigment melanin collects in one place and, as a result, lets dark spots appear.

However, the rough subdivision into various aging stages of skin aging illustrated above is not applicable to every human. In particular, the lifestyle of the individual, and his or her ethnicity, has a decisive influence on the development of the aforementioned features, and so this may result in a difference between the true age and the skin age.

Regular application of cosmetic care products brings about an improvement in the skin structure and the appearance, more particularly the reduction of wrinkles and pigmentation irregularities. Hence, the cosmetics industry supplies appropriate application instructions with its products, which also include instructions in respect of the age group for which the product is suitable.

If the true age of the user and his or her skin age differ, the consumer is misinformed by the application instructions and would select a product that is unsuitable for his or her skin age.

SUMMARY OF THE INVENTION

It is therefore an object of the method according to the invention to determine and display the age of the skin on the basis of an image of a selected region of skin or an image of at least one finger nail, or to supply a recommendation for cosmetic products on the basis of the determined age.

According to the invention, the age of the skin is determined by virtue of capturing a predetermined area of skin, e.g. the back of the hand or at least one finger nail, by optoelectronic means. The image data arising when the skin section is captured is stored in a buffer. Subsequently, image analysis is used to determine the color distribution, more particularly the ratio between dark and light regions and/or the color space, more particularly the ratio between the lightest and darkest point. Here, the determination is brought about in an integrative fashion, with the result likewise being stored in a buffer.

Within the meaning of the invention, the age of the skin is determined using the following steps:
a) optoelectronic capture of an area of skin using a digital camera unit (DKE),
   wherein the area of skin to be captured is additionally illuminated by a light source (LQ),
   wherein the digital camera unit has a cross-polarization unit (KPE),
b) storing the image in a buffer (MEM),
c) processing the image by means of a microprocessor-controlled image processing unit (mBVE),
   wherein the mBVE accesses the image stored in the buffer, isolates the B channel of the RGB image and calculates a grayscale value image in a first step and
   establishes the mean grayscale value from the grayscale value image and buffers it as "color" parameter in a second step,
   calculates the standard deviation from the grayscale value histogram and buffers it as "evenness" parameter in a third step or in a work process parallel to the second step,
d) calculating the age of the skin using the color/age-dependence correlation formula (FAF) based on the color, and/or
e) calculating the age of the skin using the evenness/age-dependence formula (EAF) based on the evenness, and
f) outputting and/or visualizing the value for the age of the skin or using the value for the age of the skin in order to recommend a product.

BRIEF DESCRIPTION OF THE DRAWINGS

The present invention is further described in the detailed description which follows, in reference to the plurality of drawings by way of non-limiting examples of exemplary embodiments of the present invention, and wherein:

1a schematically shows a design that is suitable for carrying out the method according to the invention;

FIG. 3b is a graph showing the evenness (color distribution) as a function of the age.

DETAILED DESCRIPTION OF THE PRESENT INVENTION

Figure 1A:
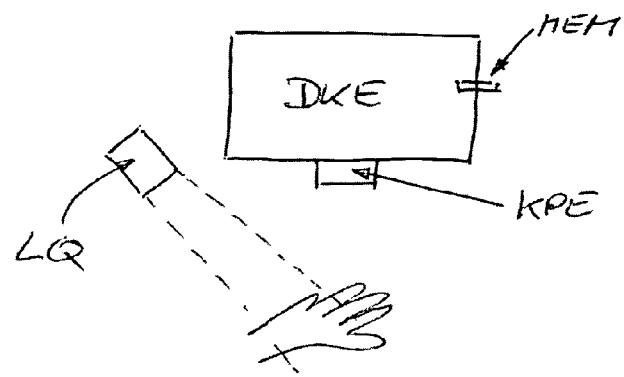
FIG. 1b schematically shows a device for image analysis with a microprocessor-controlled image processing unit (mBVE)

The optoelectronic capture is preferably brought about as a photographic recording. The illumination is preferably brought about in a directed manner.

The formulae for color/age-dependence correlation and evenness/age-dependence correlation, used in the method according to the invention, are determined experimentally. To this end, the values for color and evenness according to the aforementioned method steps a) to c) are determined and "correlated" graphically or computationally using a sufficiently large sample of subjects, which is broadly distributed in terms of age. The result is a mathematical function, the FAF and EAF, respectively. The FAF and EAF can be used to calculate the age of the skin in method steps d) and e) from the measured color and evenness.

The age to be output is preferably determined (calculated) by averaging the results from method steps d) and e).

The utilized correlation methods are based on regression analyses as described in e.g. "Taschenbuch der Mathematik" [Handbook of mathematics] by Ilja N. Bronstein and K. A. Semendjajew, and take into account to a sufficient extent the biologically given distribution of the parameter(s).

In the last step, step f), of the method according to the invention, the subject (the user or consumer at the POS) is notified of the measurement result, i.e. the calculated age of the skin or a product recommendation.

According to the invention, the age of the skin can advantageously be notified in the form of speech output or in a visualized manner. A visual output on a display or a purpose-made printout is particularly advantageous.

Examinations have shown that both the color and the even skin tone (uniformity of the color distribution) change with age. With increasing age, the skin darkens and becomes less uniform. By contrast, a dark and uniform skin indicates the tanning status or the ethnicity. An "uneven skin tone" caused by freckles or liver spots is not meaningful enough on its own for age determination because there is a greater contrast in the case of a light base tone or skin type, and so the uneven skin tone would be overinterpreted, leading to an age that is too high.

In order to side-step errors caused by such influences, it is advantageous to use both the color and evenness, or the age calculated from color and evenness, for determining the age of the skin to be output.

Here, the simplest option is the application of a linear correlation. However, in place of the linear correlation, it is particularly advantageous to apply a mathematical or complex model in which the evenness (color distribution) is weighted more strongly in the case of strong pigmentation than in the case of a lighter skin color. The use of a neural network, the accuracy of which increases with increasing number of subjects, is also an outstanding method.

It is also within the meaning of the method according to the invention for information to be queried before product recommendations are output such that this information can likewise be included in the product selection. It is particularly advantageous for the true age and/or the ethnicity and/or the sun exposure/tanning and/or the personal appraisal of the state of the skin to be queried.

In particular, the personal appraisal of the state of the skin, e.g. dry skin or normal skin or fatty skin or acne, can be an important indication for restricting the number of products to be recommended.

Further indications for a correct product selection are obtained if the skin moisture and/or the shine of the skin are determined in addition to the color and evenness parameters.

Moreover, it is advantageous to analyze two different regions of the skin in order to obtain further information in respect of the tan of the skin or the ethnicity. By way of example, to this end, and this is particularly advantageous within the meaning of the invention, the basic analysis for an area of skin could take place on the back of the hand. As an additional analysis, an area of skin on the palm of the hand would be analyzed simultaneously or thereafter. The difference in brightness makes it possible to derive whether the subject is tanned as a result of exposure to the sun or whether said subject belongs to a dark phototype (e.g. IV, V or VI).

On the basis of different tanning of the back of the hand and the palm of the hand, it is possible to determine the extent to which this tan artificially arose due to solarium use and not as a result of ethnic influences. In the case of solarium tanning, the tanning difference between the palm of the hand and back of the hand is smaller than in the case of persons with a dark skin color.

The method according to the invention can be carried out by using individual devices or by means of a device in which all subunits required to carry out the method steps are integrated (combined).

Such an integrated device should be referred to as an age scanner and it could be used directly by the customer at e.g. the point of sale in order to obtain help when selecting a product.

The recordings are captured by means of a high-resolution digital camera which is advantageously directly activated by software. Advantageously, storing the image as a native data record in the RAW data format would be conceivable; however, the use of another data format with a lossless or low compression rate is also feasible.

In order to exclude the influence of surroundings, illumination by cross-polarized light is advantageous. By way of example, suitable light sources include diode matrix lamps or electronic flashes (gas discharge flash equipment), in particular in conjunction with aids such as soft boxes and diffusers.

The age of the skin or the product recommendation can be visualized by means of a display unit or a printout. By way of example, LCD matrix displays, 7-segment displays, alphanumerical displays, dot matrix displays, TFT displays, FTN displays and tube monitors are suitable for the display. TFT displays are preferred due to their low energy consumption and appealing display. It is particularly preferred for the displays to have touch-screen functionality, by means of which interaction with the user is possible in addition to outputting the measurement results or the product recommendation only.

Advantageously, e.g. three products are in each case displayed on the visualization unit or printed onto a recommendation slip by means of a suitable technical method, or immediate delivery of the product is made possible by means of a vending machine. In one advantageous embodiment, in addition to the product specifications, it is also possible to output additional product information and/or, additionally, to query additional communication queries such as e.g. the email address of the user.

A wireless communication (e.g. by IR, Bluetooth or SMS) of the result to a cellular telephone of the customer is also within the meaning of the invention.

In the following text, the method according to the invention and a device suitable for carrying out the method are described on the basis of an exemplary embodiment. However, the invention should not be restricted to the exemplary embodiment, which only serves as a visual support for the description.

FIG. 1a schematically shows a design that is suitable for carrying out the method according to the invention. The digital camera unit (DKE) is used to make a photographic recording of an area of skin, in this case the back of the hand, which is additionally illuminated by a light source (LQ). The recording is stored on a memory chip, the buffer (MEM). The DKE is equipped with a cross-polarization unit (KPE), the use of which masks the surface structure of the skin to a great extent by optical means, and so skin unevenness and skin color emerge more clearly.

Figure 1B:
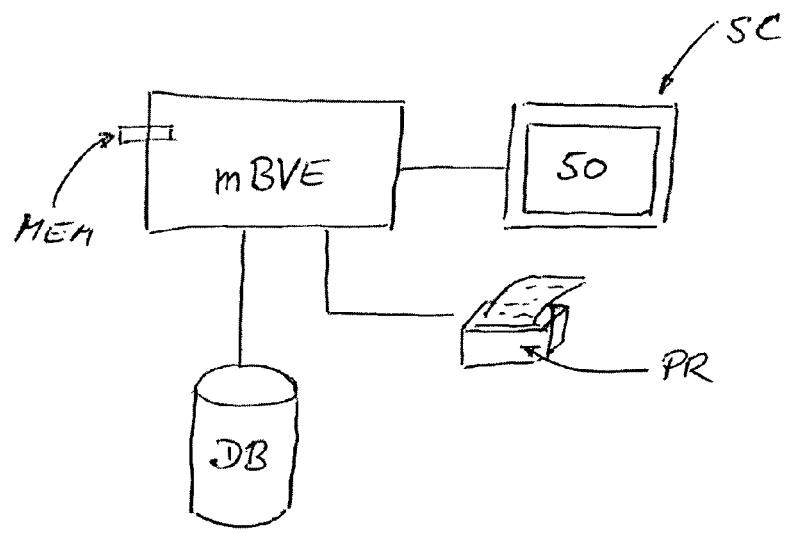

FIG. 1b schematically shows a device for image analysis with a microprocessor-controlled image processing unit (mBVE). The recording stored in the buffer (MEM) is to this end connected to the mBVE such that the nMBV can access the stored image.

In the simplest case, the mBVE can be a normal computer, on which steps c) to f) of the method can be executed by means of image analysis software.

The algorithms for determining the color parameter and the evenness parameter are already known from the prior art since these arise from statistical/mathematical fundamentals, as can be looked up in e.g. the section on regression analysis in "Taschenbuch der Mathematik" [Handbook of mathematics] by Ilja N. Bronstein and K. A. Semendjajew. The age of the skin in the photographed area of skin is subsequently determined with the aid of the color/age-dependence correlation formula (FAF), based on the color, and the evenness/age-dependence formula (EAF), based on the evenness. The calculated age of the skin is output on the display unit (SC). In a more complicated variant, the calculated age of the skin, together with a database (DB) containing information in respect of products in conjunction with the range of the age of the skin for which the products are suitable, is used to seek out those products that can be considered for the measured age of the skin. The result of the database query can be visualized for the consumer on a display unit or as a printout (PR).

Figure 2:
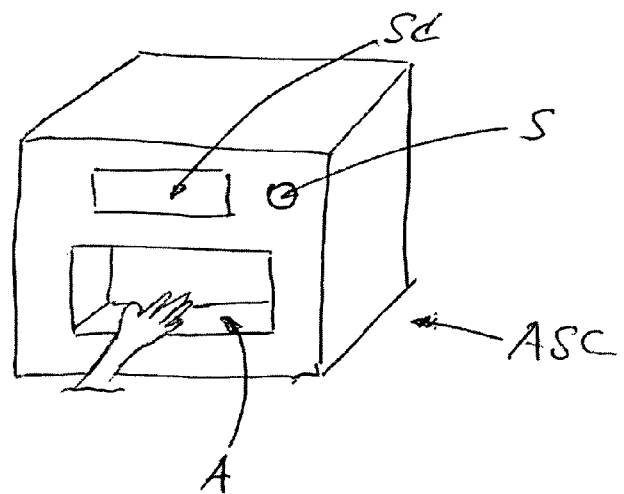
FIG. 2 shows an exemplary integrated piece of equipment (age scanner) (ASC)

FIG. 2 shows, in an exemplary fashion, an integrated piece of equipment (age scanner) (ASC), which, in principle, comprises the components illustrated in FIG. 1. In order to determine the age, the consumer places his or her hand on the bearing surface (A). Various scenarios are suitable for starting the photographic recording. The simplest option for starting the recording is that the consumer starts the recording by actuating a start switch (S). However, it is more elegant and particularly advantageous for the recording to be started automatically; to this end, it is not just a single image that is recorded, but the hand surface is filmed as soon as the bearing surface is touched or loaded. Detection by means of a photoelectric sensor or a thermal sensor is also possible. One image from the sequence of individual frames of the film is used for further processing. It is advantageous to use more than one image for separate evaluation because averaging over a number of color values and evenness values leads to a more significant determination of age.

The calculated age of the skin, or the product recommendation established by means of the database, is visualized for the consumer on a display unit (SC).

Figure 3A:
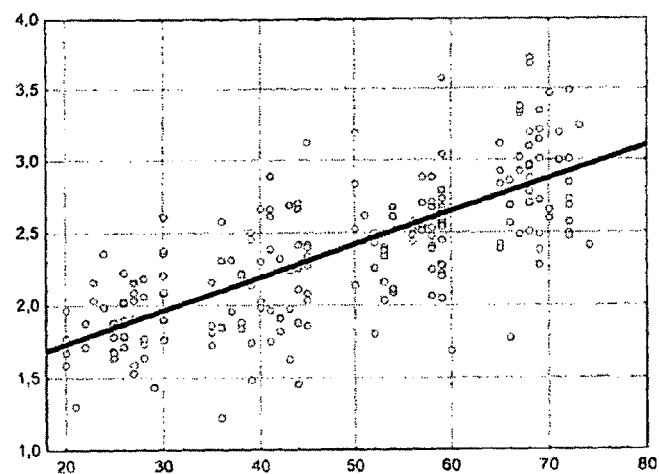
FIG. 3a is a graph showing the dependence of the color on the age.
Figure 36:
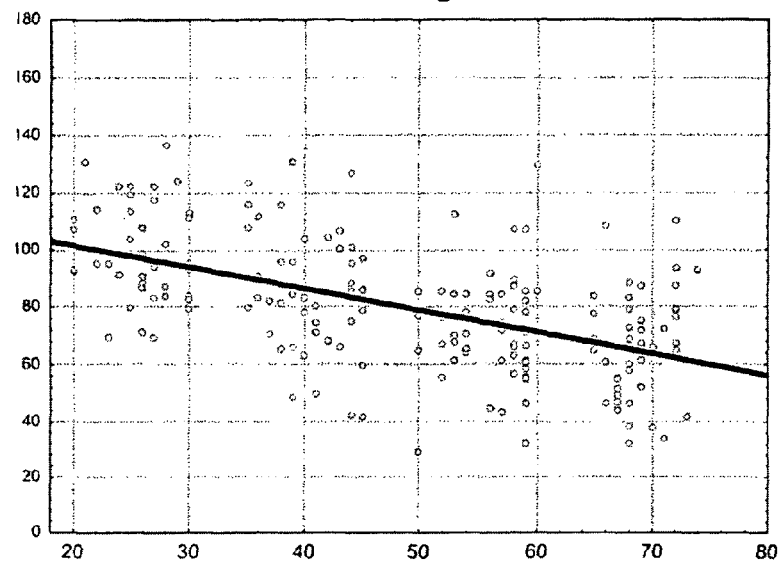

FIG. 3 shows, in an exemplary fashion, the evaluation of a measured collective, more particularly the dependence of the color on the age (FIG. 3a) and the evenness (color distribution) as a function of the age (FIG. 3b), with the age being plotted on the abscissa in each case and the evenness (3b) or color (3a) being plotted on the ordinate.

A linear regression leads to the following color/age-dependence correlation formula (FAF):

$$Age = 116.65 - 0.76 * color,$$

and to the following evenness/age-dependence formula (EAF):

$$Age = 1.25 + 0.02 * evenness.$$

What is claimed is:

1. A method for determining the age of human skin, wherein the method comprises:
    a) optoelectronically capturing an area of skin by using a digital camera unit (DKE) having a cross-polarization unit, the area of skin to be captured being illuminated by a light source (LQ) to form an image
    b) storing the image obtained according to a) in a buffer,
    c) processing the stored image by means of a microprocessor-controlled image processing unit (mBVE), wherein the mBVE
        accesses the image stored in the buffer,
        isolates B channel of an RGB image and calculates a grayscale value image in a first step and
        establishes a mean grayscale value from a grayscale value image and buffers it as "color" parameter in a second step,
        calculates a standard deviation from the grayscale value histogram and buffers it as "evenness" parameter in a third step or in a work process parallel to the second step,
    d) calculating the age of the skin using a color/age-dependence correlation formula (FAF) based on color,
    e) calculating the age of the skin using an evenness/age-dependence formula (EAF) based on evenness, and
    f) outputting a value for the age of the skin or using a value for the age of the skin (HA) to recommend a product.

2. The method of claim 1, wherein a) is brought about as a photographic recording.

3. The method of claim 1, wherein illumination using the LQ of the area of skin to be photographed is brought about in a directed fashion.

4. The method of claim 1, wherein more than one photographic recording using the DKE is used for evaluation purposes.

5. The method of claim 1, wherein an output of a measured age of the skin is at least one of visualized and brought about as speech output.

6. The method of claim 1, wherein the measured age (HA) is used to make product suggestions matched to this age, a selection being made from a range of products stored in a database.

7. The method of claim 6, wherein true age is included when considering the product selection and an intermediate value between measured age and true age is used for product selection.

8. The method of claim 7, wherein a mean value between true age and measured age is used for product selection.

9. The method of claim 1, wherein at least one of color and evenness of two different body regions is used for calculating the age of the skin.

10. The method of claim 9, wherein at least one of color and evenness of a back of a hand and a palm of the hand are used for calculating the age of the skin.

11. The method of claim 1, wherein a formula used to calculate FAF and EAF is determined from a collective of measurement values of color depending on true age for the FAF and evenness depending on the age for EAF.

12. A device for determining the age of the skin according to the method of claim 1, wherein the device comprises a digital camera unit with a cross-polarization unit for optoelectronic capture of an area of skin, a buffer for buffering at least one photographic recording, and a microprocessor-controlled image processing unit for evaluating the at least one photographic recording.

13. The device of claim 12, wherein the optoelectronic capture is brought about as a photographic recording.

14. The device of claim 12, wherein the device further comprises a display or an indicator.

15. The device of claim 12, wherein the device further comprises a speech output unit.

16. The device of claim 12, wherein the device further comprises a light source.

17. The device of claim 12, wherein the device further comprises a database with product information and wherein at least one of an age reference and a specification relating to the age of the skin for which the product is suitable are stored with products.

* * * * *